United States Patent [19]
Yamamoto et al.

[11] Patent Number: 5,427,838
[45] Date of Patent: Jun. 27, 1995

[54] FLEXIBLE PLASTIC SHEET HAVING A RIB-STRUCTURE

[75] Inventors: Masamitsu Yamamoto, Kawanoe; Yagoro Yagi, Ohtsu; Masaki Murakami, Kawanoe, all of Japan

[73] Assignee: Uni-Charm Corporation, Ehime, Japan

[21] Appl. No.: 84,247

[22] PCT Filed: Nov. 6, 1991

[86] PCT No.: PCT/JP91/01521

§ 371 Date: Jul. 1, 1993

§ 102(e) Date: Jul. 1, 1993

[87] PCT Pub. No.: 93/08778

PCT Pub. Date: May 13, 1993

[51] Int. Cl.$^6$ .............................................. B32B 3/00
[52] U.S. Cl. .................... 428/167; 428/141; 428/169
[58] Field of Search ............... 428/167, 105, 156, 120, 428/141, 152, 169, 170, 192; 264/293

[56] References Cited

U.S. PATENT DOCUMENTS

| | | | |
|---|---|---|---|
| 4,342,314 | 8/1982 | Radel et al. ........................ | 428/131 |
| 4,376,147 | 3/1983 | Byrne et al. ........................ | 428/167 |
| 4,546,029 | 10/1985 | Cancio et al. ...................... | 428/141 |
| 4,609,518 | 9/1986 | Curro .................................. | 264/504 |
| 4,710,185 | 12/1987 | Sneyd ................................. | 604/372 |
| 4,859,519 | 8/1989 | Cabe et al. ......................... | 428/131 |
| 5,143,774 | 9/1992 | Cancio et al. ...................... | 428/169 |

FOREIGN PATENT DOCUMENTS

| | | |
|---|---|---|
| 0313766 | 5/1989 | European Pat. Off. . |
| 58-19252 | 2/1983 | Japan . |
| WO91/03367 | 3/1991 | WIPO . |

*Primary Examiner*—Donald J. Loney
*Attorney, Agent, or Firm*—Lowe, Price, LeBlanc & Becker

[57] ABSTRACT

Here is disclosed a flexible plastic sheet comprising a plurality of first direction ribs ($Y_1, Y_2 \ldots$) each having opposite sides (12, 13) extending in the first direction (Y) and curved downward crossing a plurality of second direction ribs ($X_1, X_2 \ldots$) each having opposite sides (14, 15) extending in the second direction (X) and curved downward. The sheet is continuous in an area surrounded by each pair of adjacent first direction ribs and each pair of adjacent second direction ribs which cross the pair of adjacent first direction ribs. At each crossing ($C_1, C_2, C_3, C_4$), one of the ribs bulges upward and the opposite side edges of this rib are connected to the top of the other rib. The plastic sheet of this invention is featured by less gloss and less sticky touch, and is preferably used as a liquid-impermeable backsheet of a disposable hygienic wearable article.

5 Claims, 5 Drawing Sheets

FLEXIBLE PLASTIC SHEET HAVING A RIB-STRUCTURE

TECHNICAL FIELD OF THE INVENTION

The present invention relates to a flexible plastic sheet having an appearance of a woven fabric and suitable for use as a liquid-impermeable backsheet which is one of the important components of a disposable hygienic wearing article.

BACKGROUND OF THE INVENTION

Flexible plastic sheets inclusive of thermoplastic film usually have a somewhat slimy gloss and a sticky touch characterizing conventional plastic sheets, which are disliked by users in some applications of such sheets. To alleviate such gloss and to improve the touch of the sheet, several techniques have already been known, for example, a technique by which the sheet surface is embossed to take such gloss off and simultaneously to provide the surface with irregularities, and a technique by which a third ingredient is previously mixed into raw material for the sheet so that desired alleviation of the gloss and improvement on the touch may be achieved on a step of sheet production.

However, these well known techniques have not been able to achieve adequate improvement in a plastic sheet particularly used for as a surface sheet in disposable hygienic wearable articles such as sanitary napkins and disposable diapers, because the gloss and feel of the plastic sheet are decisively disliked by users of such wearable articles. U.S. Pat. No. 4,342,314 discloses a technique to provide a flexible plastic sheet with a fibrous appearance and a capillary structure for improvement of appearance as well as touch. According to the technique disclosed by this patent, an appearance closely resembling woven fabric can be achieved, but its surface could be relatively smooth and therefore apt to have yet a slimy gloss even after the sheet has been treated in accordance with the disclosed technique.

Accordingly, it is a principal object of the present invention to provide a flexible plastic sheet on its surface with a plurality of ribs crossing one another so as to create an appearance like woven fabric and thereby to alleviate said undesirable gloss and to improve touch.

DISCLOSURE OF THE INVENTION

The object set forth above is achieved, according to the present invention, by a flexible plastic sheet having a rib-structure and presenting an appearance of woven fabric comprising:

a plurality of ribs extending in a first direction each having opposite side edges curved downward and a plurality of ribs extending in a second direction, each having opposite side edges curved downward so that these first and second direction ribs cross one another;

said sheet being continuous in an area defined by each pair of adjacent first direction ribs and each pair of adjacent second direction ribs crossing said pair of adjacent first direction ribs; and tops of said pair of adjacent second direction ribs being connected to the side edges of said pair of adjacent first direction ribs at first and second crossings which are adjacent and diagonally opposed to each other, on one hand, and tops of said pair of adjacent first direction ribs being connected to the side edges of said pair of adjacent second direction ribs at third and fourth crossings which are adjacent and diagonally opposed to each other, on the other hand.

According to an aspect of the invention, said pair of adjacent first direction ribs preferably include bridges connecting opposite lower edges of these ribs.

According to another aspect of the invention, said flexible plastic sheet is preferably liquid-impermeable.

Advantageous effect provided by the invention will be readily apparent from the following description.

In the flexible plastic sheet of the invention constructed as has been mentioned, the first direction ribs cross the second direction ribs and, at each crossing, one of ribs bulges upward while the other rib sinks so that the top of the latter is connected to the side edges of the former and thereby an appearance like woven fabric such as plain weave fabric or twill weave fabric is created. Said plastic sheet is continuous in the areas surrounded by the first and second direction ribs and thus there is provided a flexible, liquid-impermeable plastic sheet.

BEST MODE FOR CARRYING OUT THE INVENTION

Figure 1:
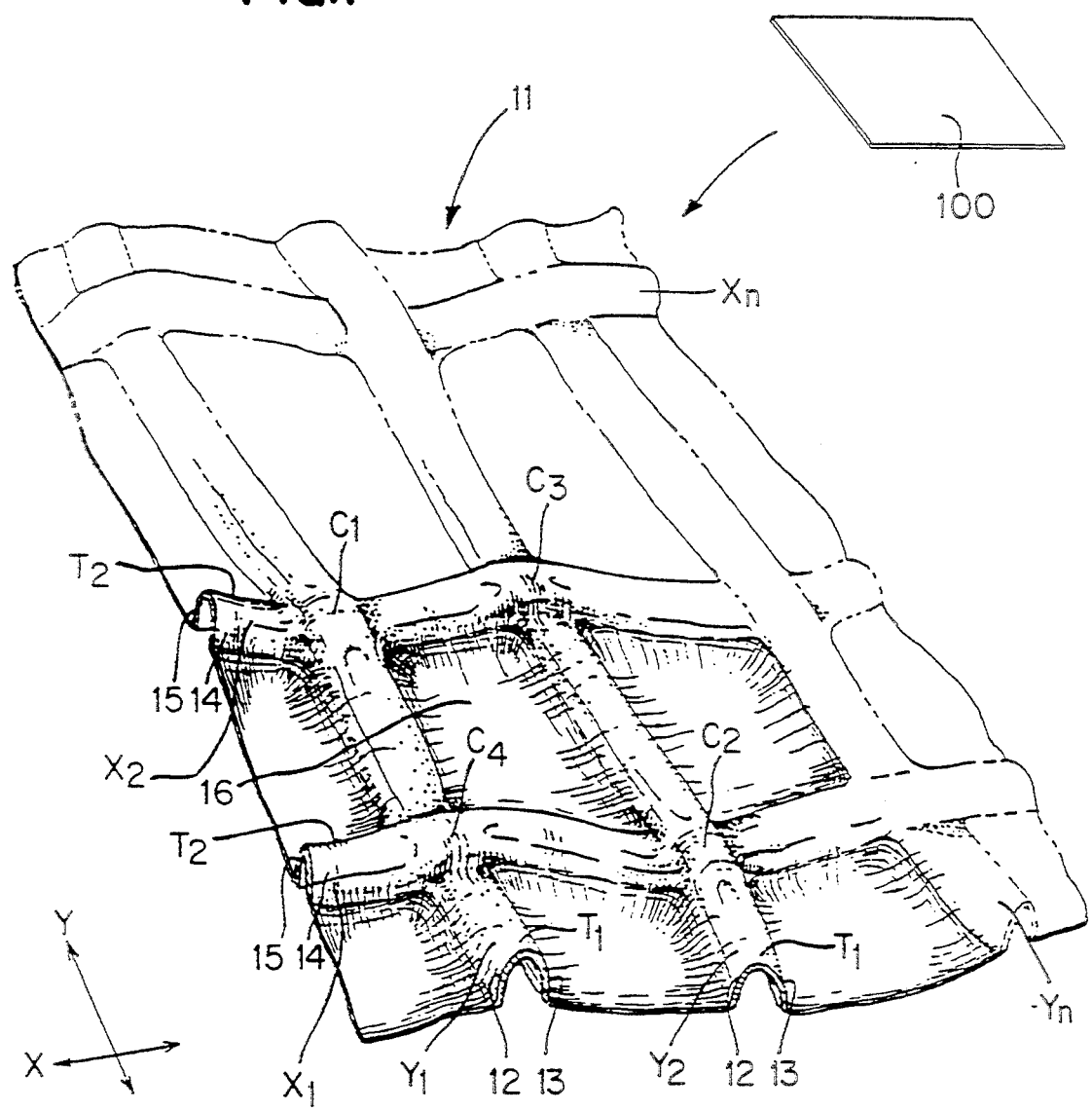
FIGS. 1 and 2 are perspective and plan views, respectively, of an embodiment of the flexible plastic sheet constructed according to the teachings of the present invention.
Figure 2:
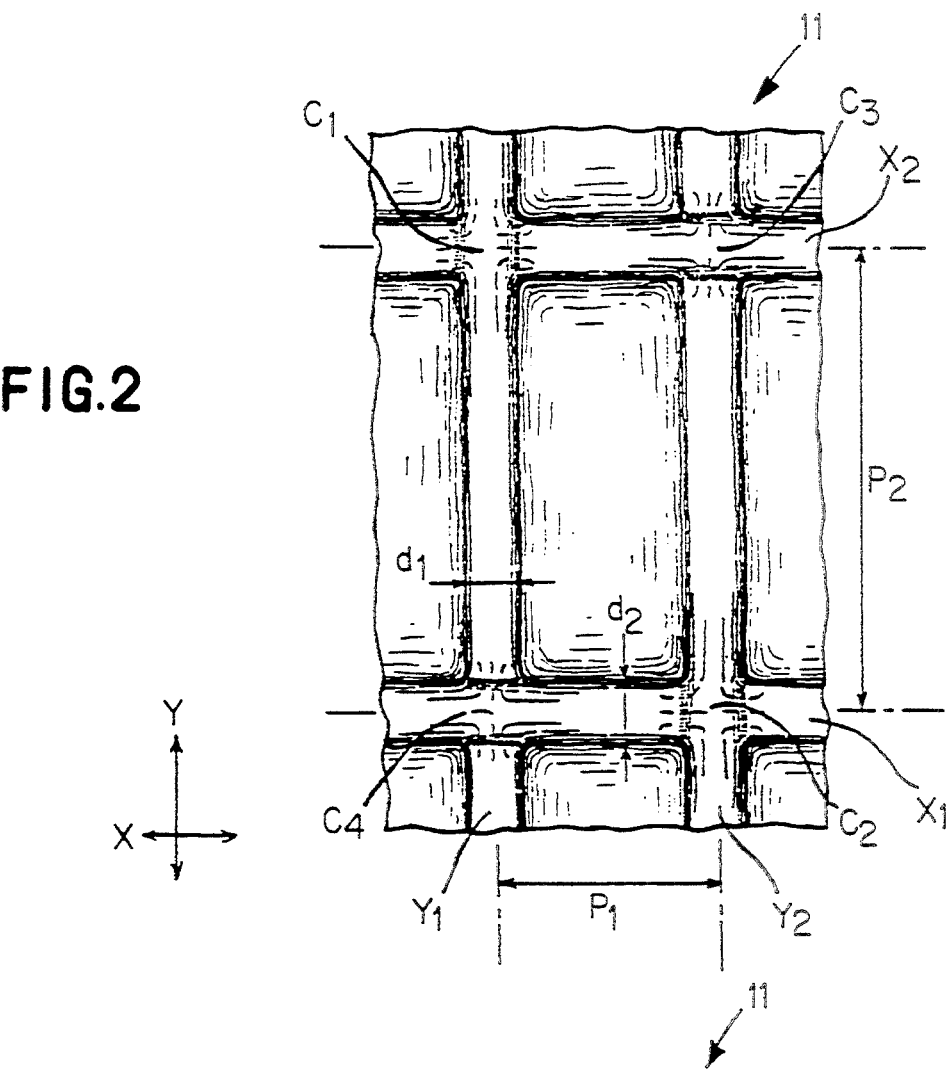

Referring to FIGS. 1 and 2, there is illustrated an embodiment of the rib-structured flexible plastic sheet 11 constructed in accordance with the teachings of the invention in perspective and plan views, respectively.

Referring particularly to FIG. 1, the sheet 11 obtained by thermoforming of thermoplastic sheet 100 has a structure comprising a plurality of ribs and areas defined by these ribs as partially represented by solid lines. Such structure may be repeatedly extended in both longitudinal and transverse directions as indicated by chain lines to obtain the complete sheet 11. The sheet 11 comprises ribs $Y_1, Y_2 \ldots Y_n$ extending in a first direction Y and ribs $X_1, X_2 \ldots X_n$ extending in a second direction X, these ribs being substantially uniform in their widths. As viewed in FIG. 1, the respective ribs are transversely curved downward so that the ribs $Y_1, Y_2$ have respective pairs of lower edges 12, 13 longitudinally extending in parallel to each other and ribs $X_1, X_2$ similarly have respective pair of lower edges 14, 15 longitudinally extending in parallel to each other. The pair of adjacent ribs $Y_1, Y_2$ extending in the first direction cross the pair of adjacent ribs $X_1, X_2$ extending in the second direction at crossings $C_1$ through $C_4$. At the first and second crossings $C_1, C_2$ which are adjacent and diagonally oppose to each other, respective tops $T_2$ of the second direction ribs $X_2, X_1$ sink and are connected to the respective side edges 12, 13 of the first direction ribs $Y_1, Y_2$, while at the third and fourth crossing $C_3, C_4$ which are also adjacent and diagonally opposed to each other, respective tops $T_1$ of the first direction ribs $Y_2$, $Y_1$ sink and are connected the respective side edges 14, 15 of the second direction ribs $X_1$, $X_2$. The pair of ribs $Y_1$, $Y_2$ cross the pair of ribs $X_1$, $X_2$ substantially at right angles and the sheet 11 is continuous in each area 16 surrounded by these two pairs of ribs. Consequently, the respective ribs create together an appearance like plain weave fabric and the sheet 11 is generally liquid-impermeable owing to such continuity.

FIG. 2 is a plan view overlooking the sheet shown by FIG. 1. Referring to this figure, the first direction ribs $Y_1$, $Y_2$ have a pitch $P_1$ and the second direction ribs $X_1$, $X_2$ have a pitch $P_2$, wherein $P_1 < P_2$, However, the sheet 11 may be constructed so as to establish a relationship of $P_1 \geq P_2$. In addition, the ribs may obliquely Cross one another, instead of crossing at right angles.

The ribs $Y_1$, $Y_2$ have a width $d_1$ and the ribs $X_1$, $X_2$ have a width $d_2$. While this specific embodiment is illustrated as the width $d_1$ is substantially equal to the width $d_2$, any one of these $d_1$ and $d_2$ may be larger than the other and each rib may be locally thinned along its longitudinally intermediate portion.

In order that the sheet 11 can have an appearance closely resembling woven fabric, the rib width $d_1$, $d_2$ should be 0.01 to 3 mm, more preferably, 0.05 to 2 mm and the number of the areas 16 defined by the ribs should be 5 to 90 per 25.4 mm, more preferably, 10 to 60 per 25.4 mm of the respective ribs. The sheet 11 may be made from a sheet 100 comprising 5 to 50 $g/m^2$, more preferably, 20 to 30 $g/m^2$ of polyethylene, polypropylene and other thermoplastic material, more preferably, a hydrophobic thermoplastic material. Use of such sheet 100 enables the sheet 11 to obtain a desired degree of flexibility. It should be understood that the term "flexibility" means the flexibility which is required by a liquid-impermeable sheet of disposable hygienic wearable article for which the use of the sheet 11 is particularly suitable. Alleviation of the somewhat slimy gloss characterizing the conventional plastic sheet, improvement of the touch and further emphasis of the woven-fabric-like appearance of the resulting sheet 11 may be effectively achieved by various countermeasures, for example, by roughening the surface of the ribs to promote a diffused reflection of incident light, irregularly varying the width of each rib, arranging the ribs at uneven pitches, appropriately coloring the sheet 100 and formulating the sheet 100 to be delustered upon thermoforming.

Figure 3:
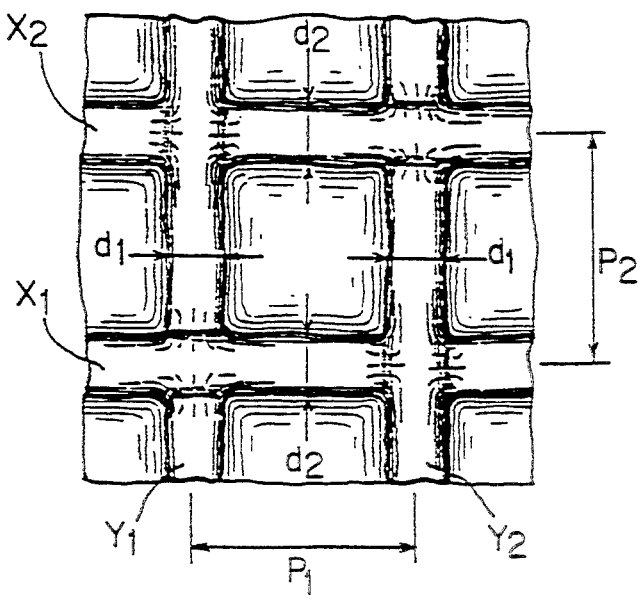
FIG. 3 is a plan view of another embodiment.

FIG. 3 is a plan view showing another embodiment of the invention. It will be apparent from this figure that the sheet 11 comprises the ribs $Y_1$, $Y_2$..., $X_1$, $X_2$... having substantially uniform widths $d_1$, $d_2$ and arranged at uniform pitches $P_1$, $P_2$, thus presenting an appearance of plain weave fabric.

Figure 4:
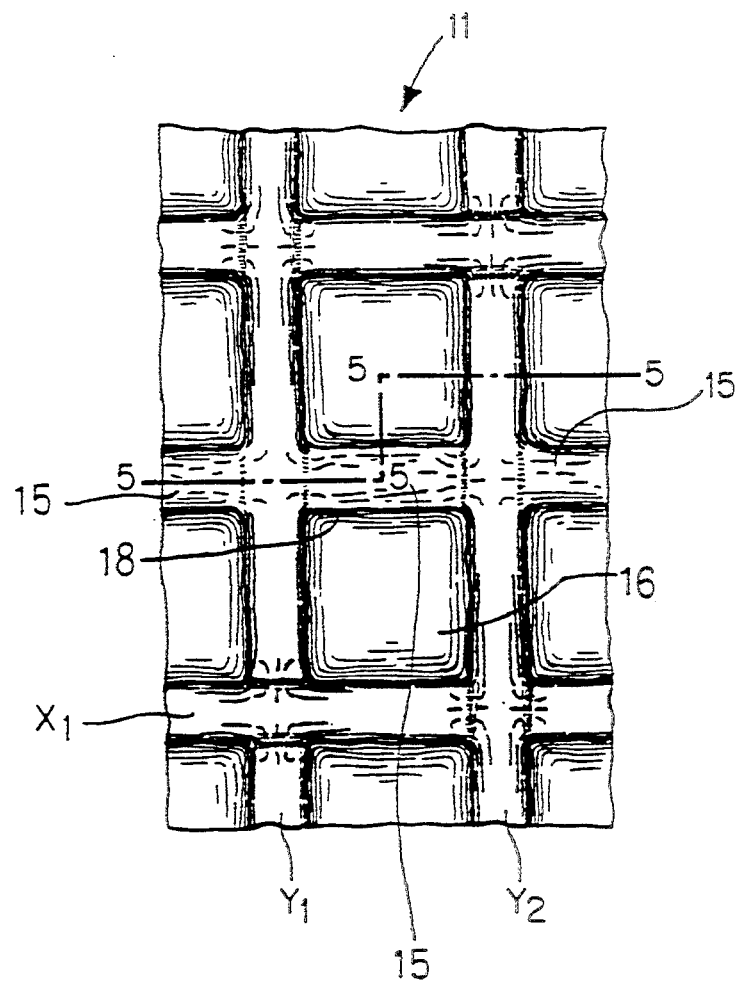
FIGS. 4 and 5 are plan and sectional views, respectively, of still another embodiment.
Figure 5:
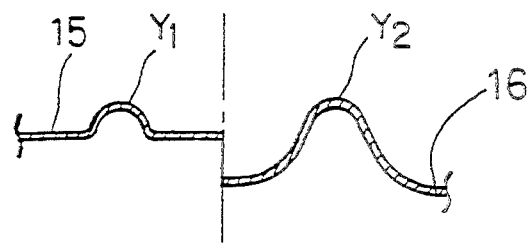

Referring to FIGS. 4 and 5, still another embodiment of the invention is illustrated in a plan view and a sectional view taken along a line 5—5 in FIG. 4, respectively. As shown, there is provided between the ribs $Y_1$, $Y_2$ in this sheet 11 a rib-like bridge 15 connecting these ribs $Y_1$, $Y_2$ to each other. Each bridge has a top which is lower than the tops $T_1$ of the ribs $Y_1$, $Y_2$ and connected to the respective side edges 12, 13 of these ribs $Y_1$, $Y_2$. This type of bridge 15 may be optionally provided between the respective pairs of adjacent ribs. When the sheet 11 contains such bridges 15, the respective bridges 15 cooperate with the adjacent ribs to create an appearance of twill weave fabric texture.

Figure 6:
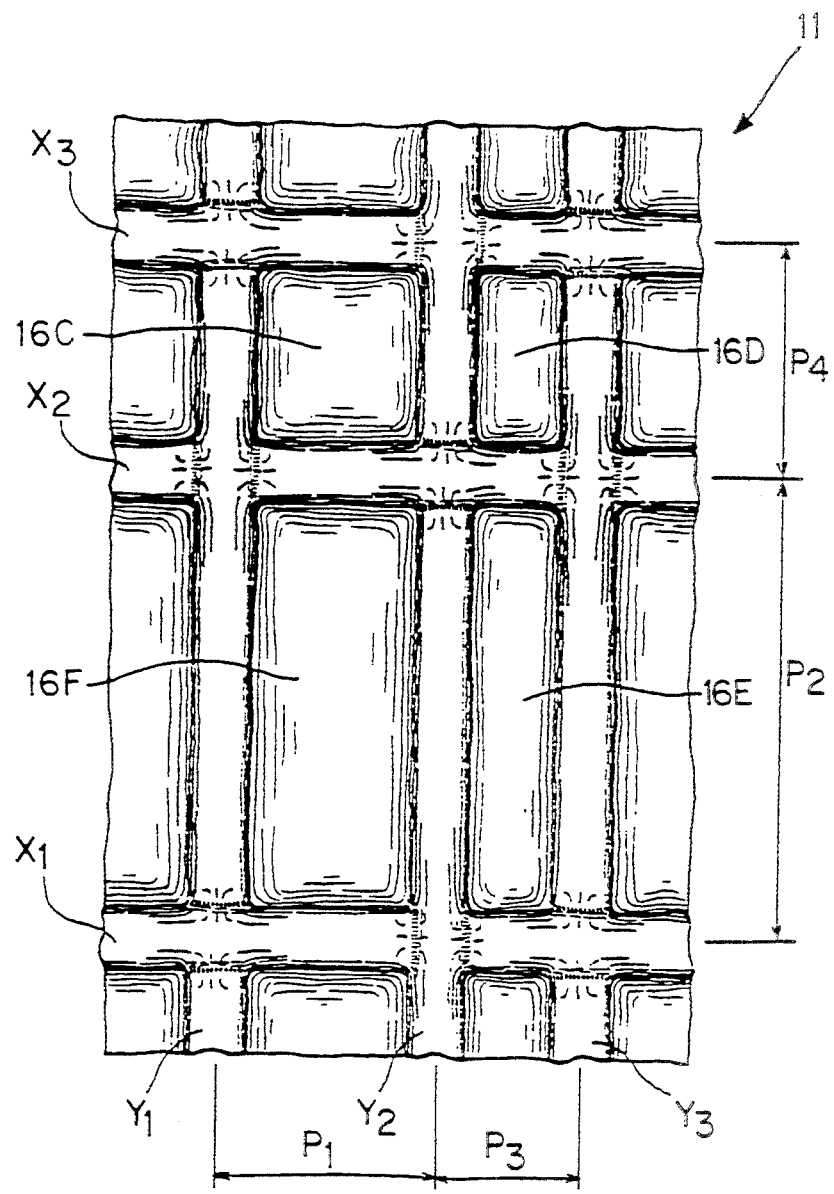
FIG. 6 is a plan view of yet another further embodiment.

Referring to FIG. 6, further another embodiment of the invention is shown in a plan view. This sheet 11 comprises first direction ribs $Y_1$, $Y_2$, $Y_3$... arranged at pitches $P_1$, $P_3$ and second direction ribs $X_1$, $X_2$, $X_3$... arranged at pitches $P_2$, $P_4$, wherein these pitches are different from one another. The ribs define areas 16C through 16F and, in the complete sheet 11, the pitches $P_1$ and $P_3$ at which the first direction ribs ($Y_1$, $Y_2$, $Y_3$) are alternately repeated and the pitches $P_2$ and $P_4$ at which the second direction ribs ($X_1$, $X_2$, $X_3$) are also alternately repeated. In this embodiment of the sheet 11 also, the rib width may be optionally varied and there may be provided between the respective pairs of adjacent ribs the bridges just as in the embodiment shown by FIG. 4.

While the embodiment of the sheet 11 as have been described hereinabove may be obtained by various methods, one of the relatively simple methods comprises steps of placing the sheet 100, while it is thermally softened, onto a top of wire net having a texture of woven fabric such as plain weave, twill weave and satin weave fabric or thermally softening the sheet 100 after it has been placed on the top of the wire net, and subjecting the sheet 100 to an effect of moderate vacuum suction controlled not to rupture the sheet 100 and provided from an underside of the wire net. Contacting the sheet 100 with the wire net texture under the effect of vacuum suction followed by rapidly cooling the sheet 100 enables this sheet to be thermoformed according to a pattern of said wire net texture into the finished sheet 11. An underside of the sheet 11 as viewed in FIG. 1 is a surface forced against the wire net. For continuous production of the sheet 11, a rotatable drum may be provided therearound with the wire net, said rotatable drum is subjected to a proper suction effect and a roll of the sheet 100 may be continuously dereeled onto said drum for thermoforming.

The wire net may be at least partially formed by stranded wire to make fine irregularities on the rib surfaces corresponding to said stranded wire.

Figure 7:
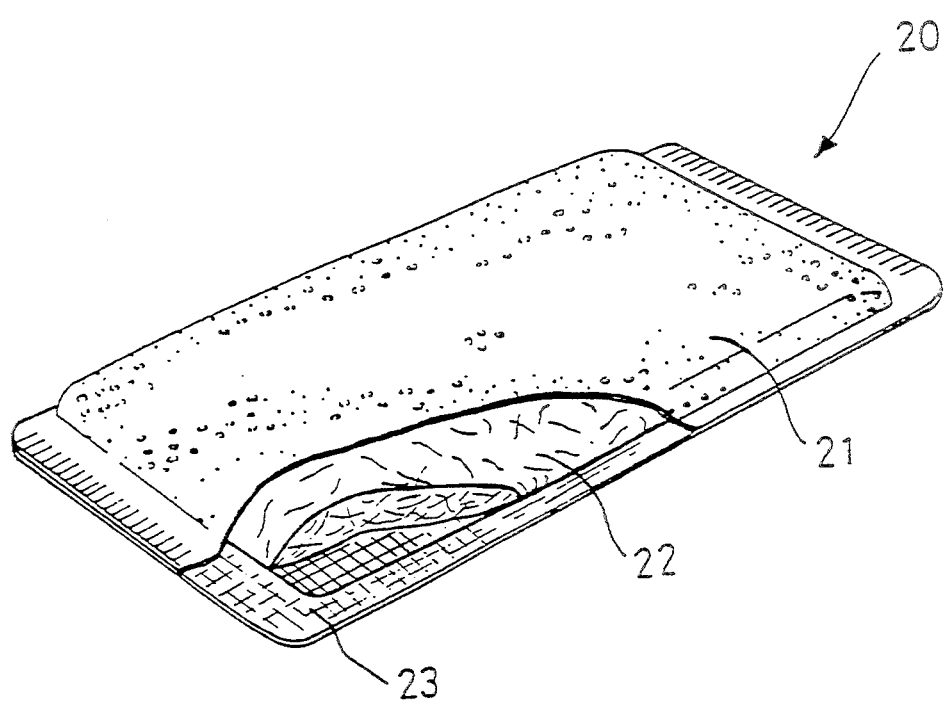
FIG. 7 is a perspective view of the plastic sheet of the invention exemplarily used as a backsheet of a sanitary napkin.

Referring to FIG. 7, a sanitary napkin 20 utilizing the sheet 11 as a backsheet 23 is shown in a perspective view partially broken away. The napkin 20 comprises an absorbent core 22 adapted to absorb and hold menstrual discharge, an air- and liquid-permeable topsheet 21 and said liquid-impermeable backsheet 23. The backsheet 23 comprises the sheet 11 shown by FIG. 1 with the rib tops being directed outward, the absorbent core 22 comprises a mixture of fluffy pulp and high water absorption polymer powder and the topsheet 21 comprises polyethylene porous film. The topsheet 21 and the backsheet 23 are bonded together along four edges of the napkin 20 so as not to leak menstrual discharge.

Industrial Usefulness

The flexible plastic sheet constructed in accordance with the teachings of the present invention is industrially useful as a liquid-impermeable backsheet of a disposable wearable article from the following viewpoints:

1) The sheet has fine bulgings and undulations on its surface on which the diffused reflection of incident light occurs to alleviate somewhat slimy gloss characterizing the conventional plastic sheet and which reduce an area of the sheet being in contact with the wearer's skin so as to eliminate somewhat sticky touch also characterizing the conventional plastic sheet.

2) The sheet presents a surface appearance resembling a texture of woven fabric such as plain weave, twill weave or the like, depending on the pattern of rib arrangement.

3) Absence of stricky touch and liquid-impermeability allows the sheet to be utilized as the leak-proof sheet for disposable hygienic wearing articles such as sanitary napkin and disposable diaper.

What is claimed is:

1. Flexible plastic sheet having a rib-structure and presenting an appearance of woven fabric, said sheet comprising:

a plurality of ribs extending in a first direction, each having opposite side portions curved downward and a plurality of ribs extending in a second direction, each having opposite side portions curved downward so that these first and second direction ribs cross one another;

said sheet being continuous in an area defined by each pair of adjacent said first direction ribs and each pair of adjacent said second direction ribs crossing said pair of adjacent first direction ribs; and the tops of said pair of adjacent second direction ribs being connected to the side portions of said pair of adjacent first direction ribs at first and second crossings which are adjacent and diagonally opposed to each other so that the tops of the first direction ribs bulge upward while the tops of the second direction ribs sink, at said first and second crossings, and tops of said pair of adjacent first direction ribs being connected to the side portions of said pair of adjacent second direction ribs at third and fourth crossings which are adjacent and diagonally opposed to each other so that the tops of the second direction ribs bulge upward while the tops of the first direction ribs sink at said third and fourth crossings.

2. Flexible plastic sheet as recited in claim 1, wherein said pair of adjacent first direction ribs include bridges connecting opposite lower portions of these ribs.

3. Flexible plastic sheet as recited in claim 1, wherein said flexible plastic sheet is liquid-impermeable.

4. Flexible plastic sheet as recited in claim 1, wherein the spacing between the first direction ribs is different from the spacing between the second direction ribs.

5. Flexible plastic sheet as recited in claim 1, wherein the spacing between a one pair of first direction ribs is different from the spacing between another pair of adjacent first direction ribs.

* * * * *